United States Patent
Messenger

(10) Patent No.: US 11,291,810 B2
(45) Date of Patent: Apr. 5, 2022

(54) RAPID EXCHANGE DILATOR FOR SHEATHLESS CATHETERIZATION

(71) Applicant: Cardinal Health Switzerland 515 Gmbh, Baar (CH)

(72) Inventor: Andrew Messenger, Pleasanton, CA (US)

(73) Assignee: Cardinal Health Switzerland 515 Gmbh, Baar (CH)

( * ) Notice: Subject to any disclaimer, the term of this patent is extended or adjusted under 35 U.S.C. 154(b) by 18 days.

(21) Appl. No.: 16/088,524

(22) PCT Filed: Mar. 30, 2016

(86) PCT No.: PCT/IB2016/000491
§ 371 (c)(1),
(2) Date: Sep. 26, 2018

(87) PCT Pub. No.: WO2017/168189
PCT Pub. Date: Oct. 5, 2017

(65) Prior Publication Data
US 2019/0374754 A1    Dec. 12, 2019

(51) Int. Cl.
*A61M 29/00* (2006.01)
*A61M 25/00* (2006.01)
(Continued)

(52) U.S. Cl.
CPC ........ *A61M 29/00* (2013.01); *A61M 25/0029* (2013.01); *A61M 25/01* (2013.01); *A61M 39/0208* (2013.01); *A61M 2025/0183* (2013.01)

(58) Field of Classification Search
CPC .. A61M 29/00; A61M 29/0029; A61M 25/01; A61M 39/0208; A61M 25/0015;
(Continued)

(56) References Cited

U.S. PATENT DOCUMENTS

| 6,102,890 A | 8/2000 | Stivland et al. |
| 8,747,428 B2 | 6/2014 | Fischell et al. |

(Continued)

FOREIGN PATENT DOCUMENTS

| CN | 103932827 A | 7/2014 |
| JP | 2004350901 A | 12/2004 |
| RU | 2195969 C2 | 1/2003 |

OTHER PUBLICATIONS

International Search Report and the Written Opinion for International Application No. PCT/IB2016/000491, dated Nov. 30, 2016, 14 pages.

(Continued)

*Primary Examiner* — Diane D Yabut
(74) *Attorney, Agent, or Firm* — ArentFox Schiff LLP

(57) ABSTRACT

A dilator for sheathless access to a vessel of a patient having a tubular distal member with a skived portion on the proximal end and a proximal member with a skived portion on the distal end. The respective skived portions overlap at a transition region and form a rapid exchange port that communicates with the lumen of the distal member. The proximal member and the distal member may be secured together with transition tubing that is coaxially disposed over the distal and of the proximal member and extends over the skived portion of the distal member within a projected circumference of the distal member.

11 Claims, 2 Drawing Sheets

(51) Int. Cl.
*A61M 25/01* (2006.01)
*A61M 39/02* (2006.01)

(58) Field of Classification Search
CPC .......... A61M 25/0023; A61M 25/0029; A61M 25/0102; A61M 2025/0183
See application file for complete search history.

(56) References Cited

U.S. PATENT DOCUMENTS

| | | |
|---|---|---|
| 8,834,510 B2 | 9/2014 | Wilson et al. |
| 2003/0125709 A1 | 7/2003 | Eidenschink et al. |
| 2009/0209941 A1 | 8/2009 | Aggerholm et al. |
| 2010/0217234 A1* | 8/2010 | Grovender ........ A61M 25/0102 604/523 |
| 2013/0237962 A1 | 9/2013 | Kawai |
| 2015/0057697 A1 | 2/2015 | Carlstrom et al. |
| 2016/0089516 A1* | 3/2016 | Sanghvi ................ A61M 29/02 604/507 |
| 2018/0064453 A1* | 3/2018 | Garrison ........... A61M 25/0067 |

OTHER PUBLICATIONS

Examination Report issued for Indian Patent Application No. 201817035822; dated Jul. 23, 2021.
Office Action issued for Japanese Patent Application No. 2021-001201; dated Oct. 26, 2021.

* cited by examiner

RAPID EXCHANGE DILATOR FOR SHEATHLESS CATHETERIZATION

FIELD OF THE PRESENT DISCLOSURE

This disclosure relates to medical devices for percutaneous endovascular procedures and, more particularly, to techniques for transradial catheterization using radial artery access.

BACKGROUND

A growing number of interventional procedures may be performed percutaneously by using one or more catheters to access treatment areas in the patient's vasculature or other regions. Although many procedures typically gain access through the femoral artery, certain access related complications are associated with this entry point. Examples of negative consequences include major bleeding complications, retroperitoneal bleeding, increased blood transfusion requirements, pseudoaneursym, difficulty in achieving hemostasis following procedure completion, required prolonged periods of immobilization, and others, any of which may be associated with a transfemoral approach. Further, the larger the entry hole in the femoral artery, the more likely the above-mentioned complications arise. Correspondingly, it may be desirable to catheterize other vessels to reduce or avoid such complications or to catheterize the femoral artery with a smaller diameter entry hole.

One suitable technique for catheterization is to gain access through the radial artery located in the patient's wrist. Transradial catheterization offers a number of benefits compared to the femoral approach, including a reduction in bleeding complications and more rapid ambulation. However, certain challenges are associated catheterization of this small size vessel. For example, spasm, pain and/or discomfort may occur. Radial artery catheterization may also lead to iatrogenic radial artery occlusion. Still further, radial catheterization limits the overall diameter of the guide catheter being used. Typically, the procedure may be limited to 6 French size in most patients, precluding the ability to perform some of the more complex coronary, peripheral endovascular and structural cardiac intervention procedures. Important predictors of radial artery spasm during transradial catheterization include a smaller size body mass index, smaller radial artery, and larger "sheath diameter to radial artery diameter index." As will be appreciated, spasm may lead to pain, irritation and inflammation, reducing the success rate of transradial catheterization. Likewise, the most important predictors of radial artery occlusion after transradial catheterization include the sex of the patient, as females typically exhibit relatively smaller vessel diameters, and the use of a 6 French (or larger) sheath. Therefore, all of these challenges result from the relatively smaller diameter of the radial artery and the corresponding increased potential for stretching, expanding or irritating the artery by inserting a device having an outer diameter larger than the inner diameter of the radial artery.

These challenges are exacerbated when a sheath is employed in the catheterization procedure. Since the guide catheter is delivered through the sheath, it necessarily must have a greater outside diameter. The outer diameter of a sheath is on average 0.60 millimeter larger than the corresponding size catheter. To address this situation, it would be desirable to employ a sheathless system. Conventional approaches may still require a radial sheath and thus are not true sheathless systems. Currently available sheathless systems are expensive and increase costs by requiring use of a new system with each guide catheter exchange. Currently available sheathless systems also require specific configurations of the guide catheter being used with the system, and correspondingly limit the choice of catheter size and shape, potentially preventing the operator from using a preferred guide catheter shape or design.

One component of a sheathless system is a dilator that is inserted through a puncture used to access the vessel in which the procedure is to be performed and then advanced through the vasculature over a guide wire. The dilator has a tapered distal tip and generally may be used to smooth the transition between the diameter of the guide wire and the outer diameter of the guide catheter being used in the procedure by gently stretching and expanding the vessel. As such, the dilator needs to have sufficient length to access distal locations in the vasculature as well have sufficient pushability and flexibility to traverse the tortuous anatomy.

To facilitate operations associated with advancing the dilator through the vasculature, it may be desirable to provide a rapid exchange port in a distal region of the dilator. The rapid exchange port communicates with a guide wire that extends to the distal end of the dilator and allows for exchange of the dilator without the necessity of employing extended length guide wires. Dilator designs that employ a tubular construction typically require that the rapid exchange port be formed by milling or an equivalent manufacturing process. These procedures are time consuming, labor intensive and therefore costly. Furthermore, the milling of the rapid exchange port creates flash around the opening that must be carefully removed and produces a significant amount of particulate waste that may be difficult to completely remove.

Accordingly, the present inventor has recognized that there is a need in the art for a dilator that allows the use of an increased diameter guide catheter by avoiding the necessity of deploying the guide catheter through a sheath. Further, the inventor has recognized that it would be desirable to facilitate the formation of a rapid exchange port. Still further, the inventor has recognized that it would be desirable to provide a dilator having good pushability while maintaining sufficient flexibility to navigate a patient's vasculature. As will be described in the following materials, this disclosure satisfies these and other needs.

SUMMARY

The present disclosure is directed to a dilator for gaining access to a vessel of a patient that includes a tubular distal member with a maximal outer diameter that extends from a distal end to a proximal end having a skived portion, a proximal member that extends from a distal end having a skived portion to a proximal end, a rapid exchange port at a transition region formed by an overlap of the skived portion of the distal end of the proximal member and the skived portion of the proximal end of the distal member and a lumen that extends between the rapid exchange port and the distal end of the distal member.

In one aspect, the rapid exchange port may be an opening formed by opposing angles of the skived portion of the distal member and the skived portion of the proximal member.

In one aspect, the proximal member may be a hypotube.

In one aspect, the proximal member may have a reduced diameter with respect to the maximal outer diameter of the distal member and the skived portion of the proximal member may overlap the skived portion of the distal member coaxially within a projected circumference of the distal member. The skived portion of the proximal member may extend distally past the skived portion of the distal member within the lumen.

In one aspect, the dilator may have transition tubing, wherein at least the skived portion of the proximal member is coaxially disposed within the transition tubing and wherein the transition tubing overlaps at least the skived portion of the distal member and is coaxially disposed within a projected circumference of the distal member. As desired, the transition tubing may extend distally past the skived portion of the distal member within the lumen.

In one aspect, the transition tubing may be heat welded to at least the skived portion of the proximal member and to at least the skived portion of the distal member.

In one aspect, the transition tubing may be intact from a proximal end to a distal end. Alternatively, a distal end of the transition tubing may be skived to correspond to the skived portion of the proximal member.

In one aspect, the distal member may be more flexible than the proximal member.

This disclosure also includes a method for gaining access to a vessel of a patient which may involve providing a dilator having a tubular distal member with a maximal outer diameter that extends from a distal end to a proximal end having a skived portion, a proximal member that extends from a distal end having a skived portion to a proximal end, a rapid exchange port at a transition region formed by an overlap of the skived portion of the distal end of the proximal member and the skived portion of the proximal end of the distal member and a lumen that extends between the rapid exchange port and the distal end of the distal member, positioning a guide wire within the vessel of the patient and advancing the dilator over the guide wire into the vessel without being inserted through a sheath so that the guide wire exits the rapid exchange port.

In one aspect, a guide catheter may be advanced over the dilator and the dilator may be removed.

In one aspect, the vessel may be a radial artery.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
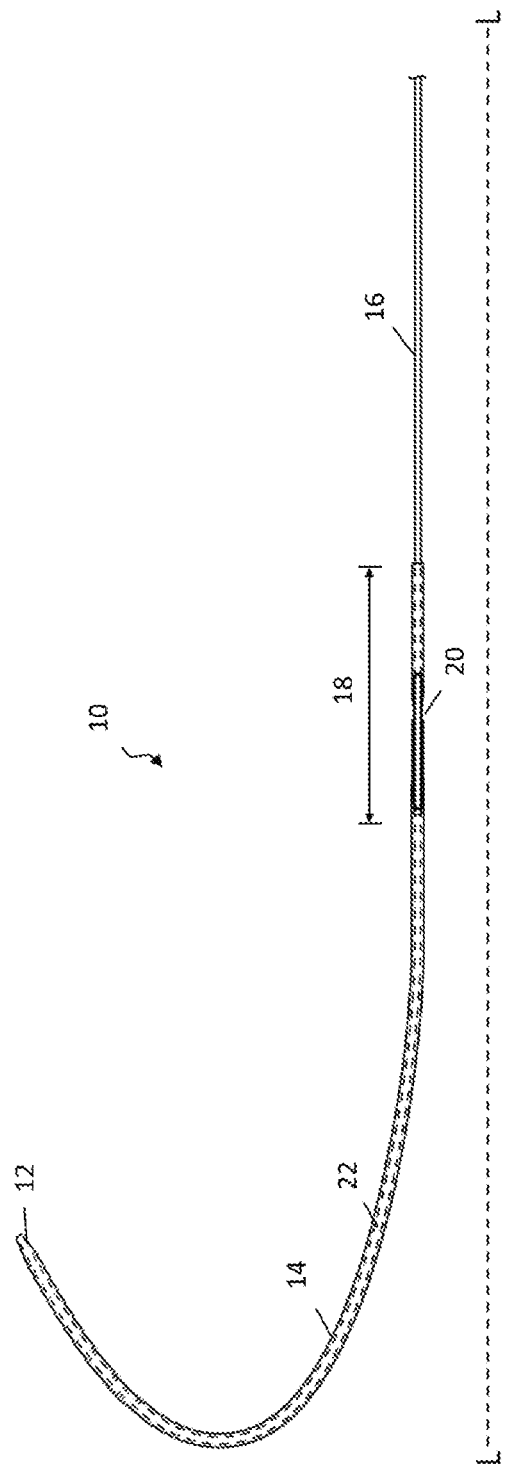
FIG. 1 is an elevation view of a dilator having a rapid exchange port for sheathless access of a vessel, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

As noted above, transradial catheterization offers significant benefits over femoral approaches due to the potential for reduced complications. By employing the techniques of this disclosure, the use of a sheath may be avoided when introducing a guide catheter into a vessel of the patient, such as the radial artery. Since a sheath is not required, a correspondingly larger diameter guide catheter may be employed. For a majority of coronary interventions, a 6 French guide catheter is required. While the median radial artery diameter ranges from 1.9 mm to 2.5 mm in different ethnic populations, conventional use of a 2.5 mm access (6 French sheath) is more likely to lead to above-mentioned problems.

While sheaths were originally designed for femoral artery access, differences in anatomy and physiology of the arteries such as radial artery and pedal artery may preclude the need to employ a sheath for access. Thus, sheathless access to an artery may be used to carry out a given catheterization task and may minimize the entry wound necessary, such as by up to two French sizes. For example, entry with a guide catheter instead of a sheath may be accomplished with a smaller overall diameter for a respective French size, such as 0.5 mm or smaller. In turn, this reduces the amount the artery is stretched and expanded, and likewise may reduce irritation, inflammation, pain and/or the chance of iatrogenic artery occlusion. As such, these techniques may be employed to reduce the size of entry in any catheterization procedure, including those for transradial, transbrachial, transfemoral and transpedal access as well as others.

The techniques of this disclosure permit transradial access, for example, while avoiding the need of using a sheath completely and is therefore a true sheathless access that may be used for diagnostic as well as all kinds of coronary intervention procedures and peripheral procedures. Notably, these techniques work in every patient with a smaller size puncture (hole) for the respective catheter size required. Most diagnostic and many interventional procedures may be performed by 1.67 mm (5 French) guide catheter with sheathless access, and, if required, the same access may be expanded to a larger size, such as a 2.00 mm (6 French) or a 2.32 mm (7 French) guide catheter. Even for such increased sizes, the use of a correspondingly larger sheath is avoided to reduce radial access size in every procedure and thereby reduce or even eliminate the limitations of radial access, such as spasm, pain, injury, radial occlusion, and the inability to perform complex interventions. Embodiments of the present disclosure may solve all the above-mentioned problems related to transradial catheterization.

To help illustrate aspects of this disclosure, an exemplary embodiment of a radial access dilator is shown schematically in FIG. 1 in an elevation view. As shown, dilator 10 is an elongated member having a longitudinal axis along the line L-L, with a tapered distal end 12 that increases to a maximal outer diameter in tubular distal member 14. The maximal outer diameter may be selected to closely conform to the inner diameter of a guide catheter to be used in a given procedure and may be substantially constant throughout distal member 14.

Distal member 14 is joined to a proximal member 16 at transition region 18, which also forms rapid exchange port 20 as described in further detail below. Distal member 14 has a lumen 22 extending from distal end 12 to rapid exchange port 20, and may have an inner diameter sized to receive a suitable guide wire, such as a 0.021" (0.58 mm) guide wire or a 0.035" (0.88 mm) guide wire for example, although other diameters may be employed depending on the intended use.

Proximal member 16 extends from transition region 18 to the proximal end of dilator 10 and may have an outer diameter that is generally constant and less than the maximal outer diameter of distal member 14. Tapered distal end 12 may be about four cm in length to provide a smooth transition with the outer diameter of the guide wire being used, to facilitate dilation of the skin, subcutaneous tissue and artery wall. If desired, some or all of dilator 10 may have a hydrophilic coating to facilitate introduction and advancement through the patient's vasculature as well as to reduce friction when a guide catheter is advanced over the dilator. In one aspect, tapered distal end 12 and proximal member 14 may have a hydrophilic coating.

As noted above, it is desirable for dilator 10 to combine flexibility with pushability, characterized by having sufficient column strength to allow the dilator to be advanced through the patient's vasculature. Accordingly, distal member 14 may be formed from a polymeric material having increased flexibility while proximal member 16 may be formed from a relatively stiffer material, and may be polymeric or metallic. In an illustrative embodiment, distal member 14 may be formed from nylon (polyamide), urethane, polypropylene, as well as polyamide co-polymers such as, for example, polyether block amides (PEBAX®), or the like and proximal member 16 may be a hypotube of stainless steel, a shape memory alloy (e.g., Nitinol or other nickel titanium alloys) or a relatively stiff polymer such as PolyEtherEther Ketone (PEEK). Proximal member 16 may also be a solid rod or wire in some embodiments. Notably, the material used for proximal member 16, such as metallic materials, may allow dilator 10 to be stored in a coiled configuration without imparting a remembered shape to proximal member 16 that would hinder advancement of dilator 10 through the patient's vasculature.

The relative dimensions of dilator 10 may be selected based on the distance between the access point and the location where the procedure is to be performed. As a representative illustration only, distal member 14 may be in the range of approximately 20-30 cm, transition region 18 may be in the range of approximately 10-15 cm and proximal member 16 may be in the range of approximately 90-120 cm. Accordingly, the reduced profile of proximal member 16 represents a significant proportion of the overall length of dilator 10 and presents less friction with the inner diameter of a guide catheter, facilitating advancement of the guide catheter over dilator 10. The overall length of dilator 10 and the respective lengths of each member may be tailored to reach a desired location in the patient's vasculature. Generally, dilator 10 may extend approximately 10-20 cm from the proximal end of the guide catheter when preloaded for introduction into the vessel. With this configuration, the proximal ends of both the guide catheter and the dilator may be manipulated during introduction and advancement. As noted, the maximal outer diameter of distal member 14 may closely correspond to the inner diameter of the guide catheter(s) being used in the procedure. For example, for a 6 French guide catheter, the maximal outer diameter may be approximately 1.80 mm, with corresponding adjustment for other sizes.

Figure 2:
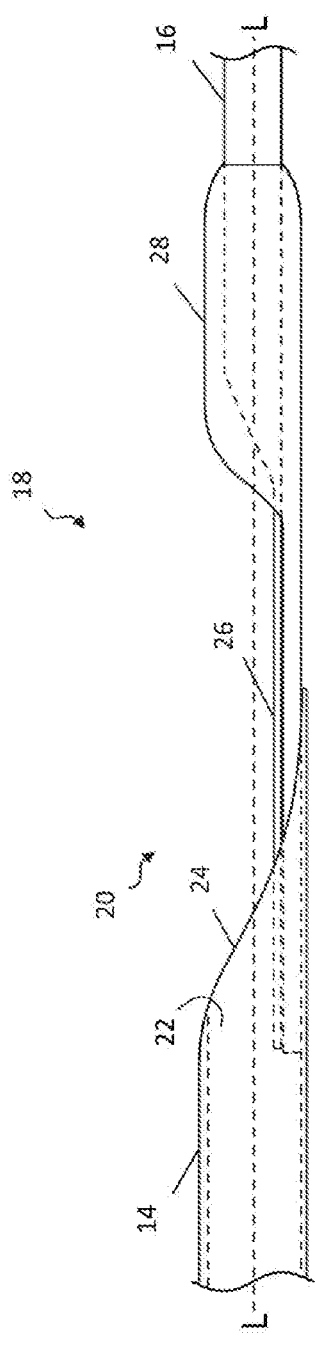
FIG. 2 is a side view of the rapid exchange port of the dilator of FIG. 1, according to one embodiment.
Figure 3:
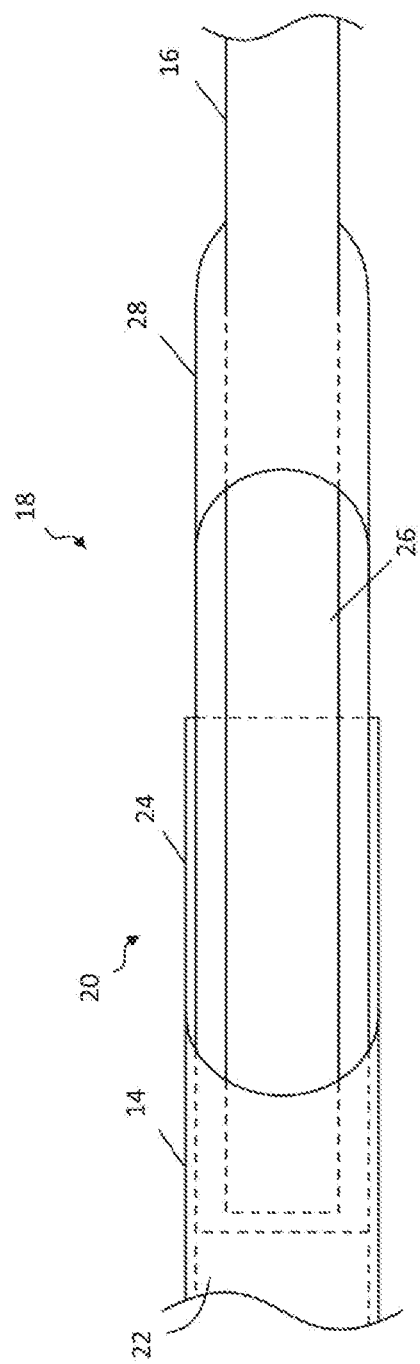
FIG. 3 is a top view of the rapid exchange port of the dilator of FIG. 1, according to one embodiment.

Transition region 18 forms rapid exchange port 20 as a result of a partial overlap of distal member 14 and proximal member 16 as schematically shown in the side view of FIG. 2, in which the longitudinal axis is indicated by the line L-L, and the top view of FIG. 3. These illustrations are not to scale, but rather are intended to show the general relationships between the respective members. As shown, material or layers of such material may be removed from tubular distal member 14 at its proximal end to form an exposed inner angular surface 24, referenced hereafter as a "skived portion" 24 having a partial circumference rather than the intact tube distal to skived portion 24. Similarly, material may be removed from proximal member 16 to form an angular, skived portion 26. In embodiments in which proximal member 16 is tubular, skived portion 26 also has a partial circumference rather than the intact tube proximal to skived portion 26. The angles of skived portions 24 and 26 may be in opposition to form rapid exchange port 20 that communicates with lumen 22 of distal member 14. In one aspect, the reduced diameter of proximal member 16 with respect to distal member 14 causes skived portion 26 to overlap skived portion 24 coaxially within a projected circumference of the intact distal member 14. Due to the amount of material removed when forming skived portions 24 and 26, the opening of rapid exchange port 20 occupies a substantial portion of the projected circumference of tubular distal member 14, allowing for easy exit of the guide wire. In comparison, a conventional port formed by milling an opening through a surface of a tube occupies less of the circumference and the user may have to bend or otherwise manipulate the tubing in order to cause the guide wire to exit.

Skived portion 26 of proximal member 16 partially overlaps skived portion 24 of distal member 14 and they may be secured together in any suitable manner. As an illustration, distal member 14 is secured to proximal member 16 by transition tubing 28 in the embodiment shown, such that the distal end of proximal member 16, including skived portion 26, is coaxially disposed within transition tubing 28. In turn, transition tubing extends coaxially within the proximal end of distal member 14. As shown, transition tubing 28 may overlap a sufficient amount of distal member 14 so that it extends distally past skived portion 24 into the intact lumen 22. However, in other embodiments, transition tubing 28 may not extend into the lumen and may only overlap skived portion 24. Likewise, the distal end of skived portion 26 may either extend past skived portion 24 as shown or may terminate before the lumen becomes intact. Transition tubing 28 may be heat welded where it overlaps with distal member 14 and proximal member 16 to secure them together. In other embodiments, adhesives or mechanical bonding as well as other known techniques may be used as desired. Transition tubing 28 may be left intact over the distal end of proximal member 16 and will conform to skived portion 26 as a result of the heat welding process or it may be skived in a similar manner. If left intact, transition tubing 28 may facilitate exit of the guide wire from rapid exchange port 20 by blocking entrance to the lumen of proximal member 16 when a tubular member is used. Transition tubing 28 may be formed from similar materials as described earlier for the distal and proximal ends (but without the metallic portion). For example, nylon (polyamide), urethane, polypropylene, as well as polyamide copolymers such as, for example, polyether block amides (PEBAX®), or a relatively stiff polymer such as PolyEtherEther Ketone (PEEK) can be used and the actual material is dependent on the intended parameters of the device. Since transition tubing interfaces with a greater amount of surface area than the overlapping skived portions 24 and 26, a reliable and secure bond may be formed. Further, transition tubing 28 provides a smooth change in flexibility between the relatively stiffer proximal member 16 and the more flexible distal member 14 while reducing the tendency to kink at the junction. In comparison, a conventional port formed by milling an opening through a surface of a tube causes discontinuous transition in flexibility and column strength and may increase the potential for kinking at the port. Still further, since transition tubing 28 and skived portion 26 of proximal member 16 lie coaxially within the profile of the maximal outer diameter of distal member 14, the attachment does not cause protrusions or disturbances that would impede advancement of dilator 10 through the patient's vasculature. It should be noted that the material used for proximal member 16 should be less flexible as compared to the material for distal member 14. One technique to ensure that this relationship is maintained during a material selection process is to measure the deflection of the proximal member 16 with a given load on a goniometer as compared to the deflection of the distal member using the same load on the goniometer.

Any suitable technique may be employed to use dilator 10 for transradial catheterization and may be extended to cover use of other sizes of guide catheters and guide wires for access to other vessel in a patient. As an illustration, transradial access is achieved by palpation or ultrasound guidance as desired. The radial artery may be punctured using a 21-gauge needle or similar apparatus. An anterior or posterior puncture can be performed by either using a bare needle or an intra-catheter venous access needle, respectively. Once pulsatile blood flow is seen, a guide wire may be inserted in the radial artery, following which the needle is removed while securing the guide wire in the radial artery lumen and hemostasis is achieved. An appropriate guide catheter that may be selected in view of the procedure being performed may be pre-loaded on dilator 10, both of which may then be advanced over the guide wire into the radial artery. After advancing a corresponding distance, the guide wire will exit from rapid exchange port 20. The relatively smooth, atraumatic transition between the maximal outer diameter portion 14 and the outer diameter of the guide catheter resulting from the close conformance of the outer diameter of the dilator and the inner diameter of the guide catheter facilitates the advancement of the guide catheter over the dilator. Once the guide catheter has been suitably advanced, such as so that its distal end is adjacent the junction between tapered distal end 12 and maximal outer diameter distal member 14, the dilator may be removed.

As will be appreciated from the above description, access to the radial artery using dilator 10 may be accomplished with at least a 0.5 mm smaller hole and a smaller intrusion into the radial artery as compared to conventional entry with a sheath. For example, a 6 French sheath will lead to 2.61 mm puncture in radial artery while using radial access dilator 10, the radial artery puncture and the maximal diameter of a device to be inserted in the artery may be reduced to approximately 2.00 mm. In this manner, most or all patients will be able to tolerate the use of a 6 French guide catheter, with considerably less trauma. Further, a 7 French guide catheter (outer diameter 2.3 mm) may be used with a greater proportion of patients, so that more complex coronary procedures and peripheral procedures may be performed. In other procedures, a 5 French guide catheter may be employed. Regardless of the size of the guide catheter, the requirement of a smaller hole and avoidance/reduction of expansion and/or irritation of the radial artery as compared to access with a sheath will reduce or eliminate, spasm, pain, inflammation and occlusion, and allow a successful transradial catheterization. By employing a relatively stiff proximal member 16, dilator 10 exhibits improved control and pushability while being advanced within the patient's vasculature. Further, the relatively more flexible distal member 14 improves navigation through the tortuous anatomy and reduces trauma. Securing distal member 14 to proximal member 16 at transition region 18 in the manner described facilitates formation of rapid exchange port 20, while maintaining column strength and providing kink resistance.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A dilator for gaining access to a vessel of a patient, comprising:
    a tubular distal member that extends along a longitudinal axis, the tubular distal member having a maximal outer diameter from a distal end to a proximal end and a skived portion;
    a proximal member that extends longitudinally from a distal end having a skived portion to a proximal end;
    transition tubing connected to the proximal member so that the proximal member is coaxially disposed within the transition tubing, wherein the transition tubing is connected to the distal member in an overlapping portion that extends coaxially within the proximal end of the distal member; and
    a rapid exchange port at a transition region formed by an overlap of the skived portion of the distal end of the proximal member and the skived portion of the proximal end of the distal member and a lumen that extends longitudinally continuously through the rapid exchange port between the proximal end of the distal member and the distal end of the proximal member.

2. The dilator of claim 1, wherein the rapid exchange port comprises an opening formed by opposing angles of the skived portion of the distal member and the skived portion of the proximal member.

3. The dilator of claim 1, wherein the proximal member comprises a hypotube.

4. The dilator of claim 1, wherein the proximal member has a reduced diameter with respect to the maximal outer diameter of the distal member and the skived portion of the proximal member overlaps the skived portion of the distal member coaxially within a projected circumference of the distal member.

5. The dilator of claim 4, wherein the skived portion of the proximal member extends distally past the skived portion of the distal member within the lumen.

6. The dilator of claim 4, wherein at least the skived portion of the proximal member is coaxially disposed within the transition tubing and wherein the transition tubing overlaps at least the skived portion of the distal member and is coaxially disposed within a projected circumference of the distal member.

7. The dilator of claim 6, wherein the transition tubing extends distally past the skived portion of the distal member within the lumen.

8. The dilator of claim 6, wherein the transition tubing is heat welded to at least the skived portion of the proximal member and to at least the skived portion of the distal member.

9. The dilator of claim 6, wherein the transition tubing is intact from a proximal end to a distal end.

10. The dilator of claim 6, wherein a distal end of the transition tubing is skived to correspond to the skived portion of the proximal member.

11. The dilator of claim 1, wherein the distal member is more flexible than the proximal member.

\* \* \* \* \*